United States Patent
Buckton et al.

(10) Patent No.: US 10,492,766 B2
(45) Date of Patent: Dec. 3, 2019

(54) METHOD AND SYSTEM FOR SNAPSHOT SUPPORT FOR REAL-TIME ULTRASOUND

(71) Applicant: General Electric Company, Schenectady, NY (US)

(72) Inventors: Daniel John Buckton, Salzburg (AT); Manfred Aichhorn, Zipf (AT); Peter Falkensammer, Zipf (AT); Thomas Huepf, Zipf (AT); Erwin Fosodeder, Zipf (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 587 days.

(21) Appl. No.: 14/549,075

(22) Filed: Nov. 20, 2014

(65) Prior Publication Data
US 2016/0143629 A1    May 26, 2016

(51) Int. Cl.
*A61B 8/14*  (2006.01)
*A61B 8/00*  (2006.01)
*A61B 8/08*  (2006.01)

(52) U.S. Cl.
CPC .............. *A61B 8/543* (2013.01); *A61B 8/486* (2013.01); *A61B 8/5207* (2013.01); *A61B 8/54* (2013.01); *A61B 8/463* (2013.01); *A61B 8/467* (2013.01)

(58) Field of Classification Search
CPC ......... A61B 8/463; A61B 8/467; A61B 8/486; A61B 8/52; A61B 8/543
See application file for complete search history.

(56) References Cited

U.S. PATENT DOCUMENTS

| | | | | |
|---|---|---|---|---|
| 5,709,210 A | * | 1/1998 | Green | A61B 5/0456 600/453 |
| 6,350,238 B1 | * | 2/2002 | Olstad | A61B 8/00 600/437 |
| 6,669,638 B1 | * | 12/2003 | Miller | A61B 8/00 600/438 |
| 2006/0052704 A1 | * | 3/2006 | Baba | A61B 8/02 600/453 |
| 2006/0058654 A1 | * | 3/2006 | Di Marco | A61B 8/00 600/437 |
| 2007/0276246 A1 | * | 11/2007 | Lin | A61B 8/00 600/444 |
| 2010/0172540 A1 | * | 7/2010 | Davis | G06F 17/30876 382/100 |
| 2014/0169766 A1 | * | 6/2014 | Yu | H04N 5/76 386/282 |

\* cited by examiner

*Primary Examiner* — Mark D Remaly
(74) *Attorney, Agent, or Firm* — McAndrews, Held & Malloy, Ltd.; Jacob Groethe; David Bates (57) ABSTRACT

Various embodiments include a system and method that provide support for acquiring secondary ultrasound image snapshots with primary real-time ultrasound image data. The method can include acquiring first image data at an ultrasound system in a primary acquisition mode based on primary acquisition mode imaging parameters. The method may include receiving a trigger to switch from the primary acquisition mode to a secondary acquisition mode. The method can include acquiring second image data at the ultrasound system in a secondary acquisition mode based on secondary acquisition mode imaging parameters in response to the trigger. The method may include displaying a replay cine sequence that includes the first image data and the second image data. The replay cine sequence can include a tag identifying the second image data in the replay cine sequence.

20 Claims, 3 Drawing Sheets

METHOD AND SYSTEM FOR SNAPSHOT SUPPORT FOR REAL-TIME ULTRASOUND

CROSS-REFERENCE TO RELATED APPLICATIONS/INCORPORATION BY REFERENCE

Not Applicable

FIELD OF THE INVENTION

Certain embodiments of the invention relate to ultrasound imaging. More specifically, certain embodiments of the invention relate to a method and system for acquiring secondary ultrasound image data, also referred to as snapshots, with primary real-time motion ultrasound image data.

BACKGROUND OF THE INVENTION

Ultrasound imaging is a medical imaging technique for imaging organs and soft tissues in a human body. Ultrasound imaging uses non-invasive high frequency sound waves to produce images, which may be viewed as static or real-time motion two-dimensional (2D) images, static three-dimensional (3D) images, and/or four-dimensional (4D) images (i.e., 3D real-time motion images).

Sonographers are under pressure to efficiently perform ultrasound examinations while fully capturing the clinical details needed to analyze a patient. The workflow of a sonographer, however, is often interrupted by adjustments needed to highlight certain aspects that cannot be readily identified in a real-time acquisition. For example, while acquiring lower quality real-time 2D or 4D image data, a sonographer may desire to intermittently acquire higher quality 2D, 3D, 4D, or spatio-temporal image correlation (STIC) style acquisition images, e.g., STIC or electronic STIC (eSTIC) images, or images of different acquisition types, such as color or B-Flow frames. To do so, sonographers typically stop acquiring the real-time 2D or 4D image data, enter scan parameters and settings for the secondary acquisition, and perform the secondary scan. Once the secondary scan is complete, the sonographer may view and interact with the secondary image(s) prior to beginning a new real-time 2D or 4D scan. This workflow with frequent interruptions for acquiring separate image acquisitions is inefficient.

Another problem exists for image review workflows. Specifically, after the ultrasound examination is complete, the separate image acquisitions may be viewable by selecting a particular image acquisition from a list of acquisitions. However, due to the frequent interruptions, a large number of acquisitions may be available, making it difficult to navigate between acquisitions and identify an acquisition of interest.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for supporting acquisition of secondary ultrasound image snapshots with primary real-time ultrasound image data, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Certain embodiments of the invention may be found in a method and system for providing support for secondary ultrasound image acquisitions with primary real-time ultrasound image data. More specifically, aspects of the present invention have the technical effect of providing support for secondary snapshot image acquisition while acquiring primary real-time motion ultrasound image data, where the ultrasound system 100 is capable of seamlessly switching between image acquisition modes to generate an integrated acquisition and/or individual acquisitions that may be viewable as one continual acquisition. For example, primary and secondary image acquisitions may be integrated into a continuous sequential acquisition viewable at a display system 134, such as shown in the replay cine display 200 illustrated in FIG. 2. The acquisitions may appear as a single replay cine sequence 220, where secondary image acquisitions may be tagged 224 to provide information as to where in the replay cine sequence 220 the secondary snapshot image acquisition(s) can be found amongst the primary real-time motion ultrasound image data. Various embodiments have the technical effect of improving image acquisition efficiency of the ultrasound system 100 by minimizing interruptions when acquiring ultrasound data in multiple image acquisition modes. Certain embodiments have the technical effect of improving visualization of image data acquired in multiple image acquisition modes by presenting the image data acquired in the different image acquisition modes as a single continual acquisition on a display system 134.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the invention, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

Figure 1:
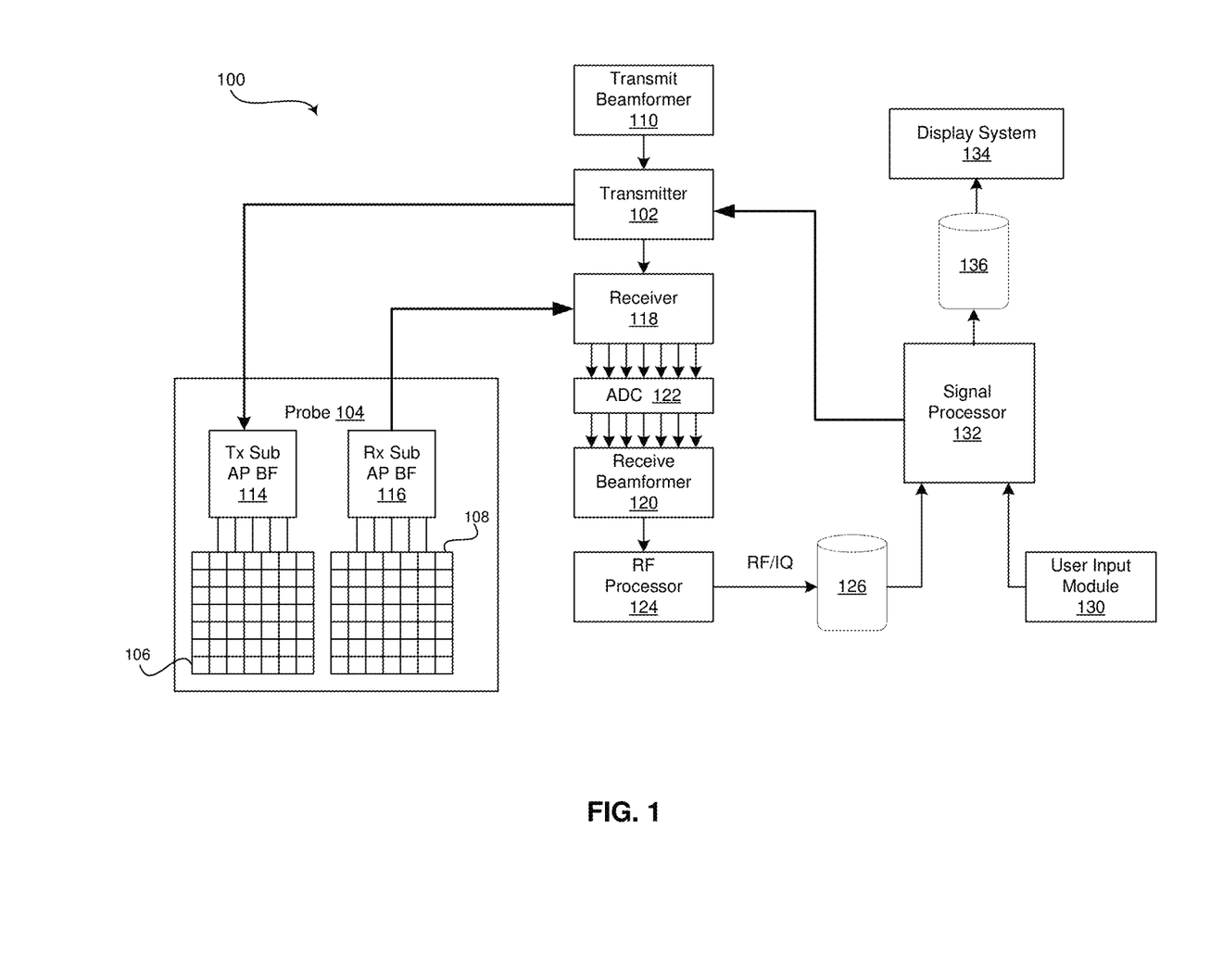
FIG. 1 is a block diagram of an exemplary ultrasound system that is operable to provide support for secondary ultrasound image acquisitions with primary real-time ultrasound image data, in accordance with an embodiment of the invention.

FIG. 1 is a block diagram of an exemplary ultrasound system 100 that is operable to provide support for secondary ultrasound image acquisitions with primary real-time ultrasound image data, in accordance with an embodiment of the invention. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an image buffer 136, and a display system 134.

The transmitter 102 may comprise suitable logic, circuitry, interfaces and/or code that may be operable to drive an ultrasound probe 104. The ultrasound probe 104 may comprise a two dimensional (2D) or three dimensional (3D) array of piezoelectric elements. The ultrasound probe 104 may comprise a group of transmit transducer elements 106 and a group of receive transducer elements 108, that normally constitute the same elements.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108. The group of receive transducer elements 108 in the ultrasound probe 104 may be operable to convert the received echoes into analog signals, undergo sub-aperture beamforming by a receive sub-aperture beamformer 116 and are then communicated to a receiver 118.

The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122. The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the invention is not limited in this regard. Accordingly, in some embodiments of the invention, the plurality of A/D converters 122 may be integrated within the receiver 118.

The receive beamformer 120 may comprise suitable logic, circuitry, interfaces and/or code that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments of the invention, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment of the invention, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, a scan mode, scan mode triggers, scan parameters, settings, configuration parameters, and the like. In an exemplary embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, and/or the display system 134.

In various embodiments, the user input module 130 may be operable to receive user input identifying a primary acquisition mode and imaging parameters corresponding to the primary acquisition mode. Examples of primary acquisition modes may include, among other things, 2D or 4D real-time motion imaging modes. The user input module 130 may be operable to receive user input identifying a secondary acquisition mode and corresponding trigger and imaging parameters for the secondary acquisition mode. The trigger may be, for example, a timer trigger, an automatic trigger, or a user trigger. A timer trigger may be defined to acquire a secondary image acquisition at various intervals, such as every one (1) second, for example. An automatic trigger may be a condition detected in the primary image data, such as when the primary image is stable and a heart rate is detected. A user trigger may be a button or other control of the user input module 130 that is set-up to switch from the primary acquisition mode to a secondary acquisition mode. Examples of secondary acquisition modes may include 2D, 3D, 4D, and/or spatio-temporal image correlation (STIC) style acquisition modes that can be higher quality than the primary acquisition mode. The secondary acquisition mode can include an acquisition type that is different than the primary acquisition type, such as a color or B-flow frame, among other things. In an exemplary embodiment, temperature limitations can be overcome by intermittently switching to the higher transmit power secondary acquisition mode. As an example, higher quality image acquisitions may increase a temperature of a probe more than lower quality image acquisitions. A cooler probe temperature may be maintained, for example, by acquiring the higher quality image acquisitions at intervals, instead of continuously.

The signal processor 132 may comprise suitable logic, circuitry, interfaces and/or code that may be operable to process the ultrasound scan data for generating an ultrasound image for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform compounding, motion tracking, and/or speckle tracking. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several seconds worth of frames of ultrasound scan data. The frames of ultrasound scan data are stored in a manner to facilitate retrieval thereof according to its order or time of acquisition. The image buffer 136 may be embodied as any known data storage medium. The acquired ultrasound scan data may additionally or alternatively be stored in an archive (not shown).

The signal processor 132 may include suitable logic, circuitry, interfaces and/or code that may be operable to process image data acquired by the ultrasound system 100 in multiple image acquisition modes. For example, based on user input received at the user input module 130, the signal processor 132 may be configured to process image data acquired in a primary acquisition mode having corresponding imaging parameters. The signal processor 132 may be configured to switch from the primary acquisition mode to process ultrasound data acquired in a secondary acquisition mode based on a user-defined trigger and imaging parameters for the secondary acquisition mode. Once the ultrasound system 100 completes the secondary ultrasound scan, the system 100 may resume acquiring image data in the primary acquisition mode. The primary and secondary image acquisitions may be displayed on the display system 134 as described, for example, with reference to FIG. 2 below.

As defined herein, the primary acquisition mode may be a 2D or 4D real-time motion imaging mode, or any suitable scan mode. The secondary acquisition modes may include 2D, 3D, 4D, STIC style acquisition modes, and the like. In various embodiments, the secondary acquisition mode may be higher quality than the primary acquisition mode. The secondary acquisition mode can include an acquisition type that is different than the primary acquisition type, such as a color or B-flow frame, among other things. Imaging parameters, depending on the acquisition mode, may include a depth setting of an ultrasound image, a width setting of an ultrasound image, ultrasound image line density, a position of a region-of-interest (ROI), a pulse-repetition-frequency (PRF) setting of the ultrasound system 100, a gain setting of the ultrasound system 100, an adaptive gain setting of the ultrasound system 100, at least one transmit focus position of the ultrasound system 100, a position of a 3D acquisition region, frame averaging, speckle reduction filtering, compounding, a number of compounding angles, or some combination. The trigger may be a timer trigger, an automatic trigger, or a user trigger. For example, a timer trigger may be defined to acquire a secondary image acquisition at pre-defined intervals. An automatic trigger may be a condition detected by the signal processor 132 when processing the primary image data. A user trigger may be a button or other control of the user input module 130 that is set-up to activate a secondary acquisition mode.

Figure 2:
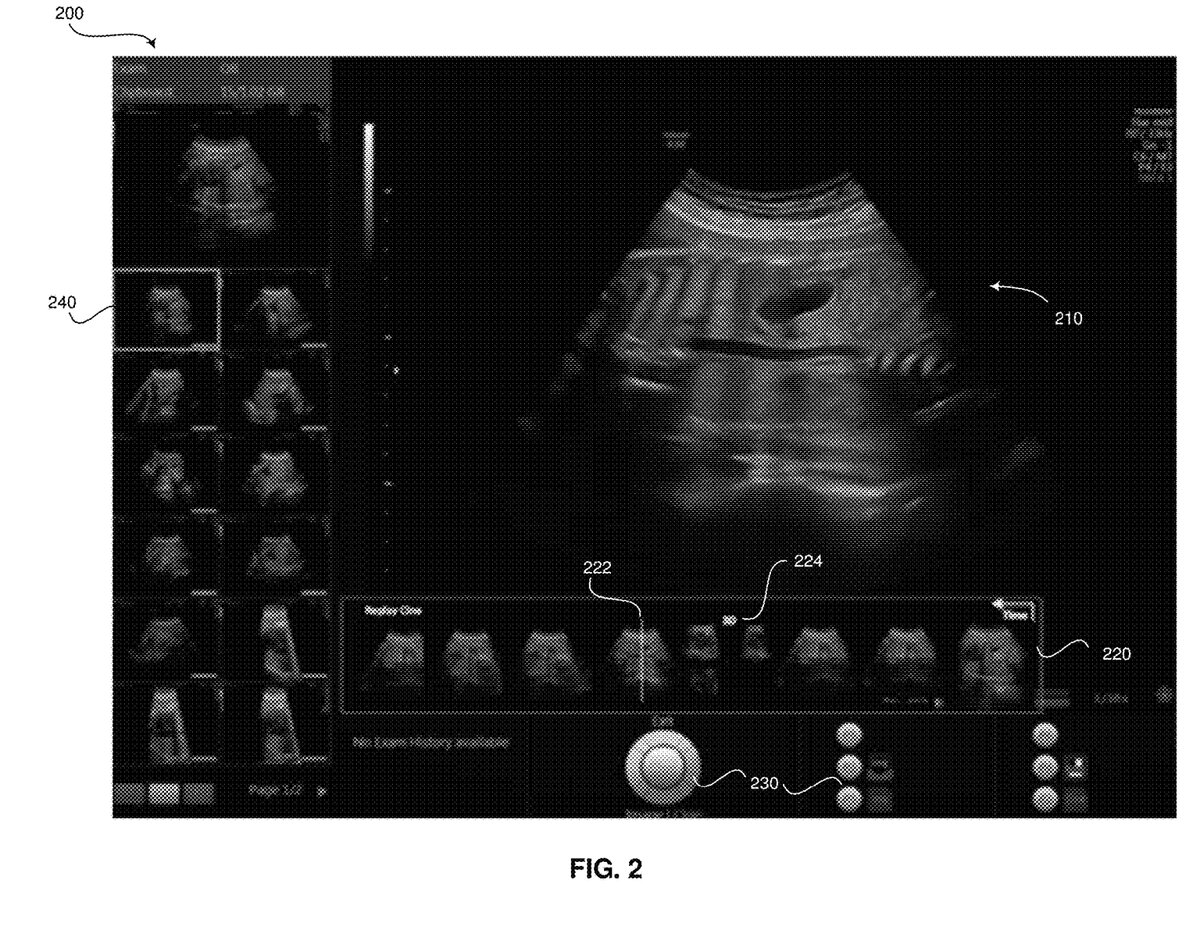
FIG. 2 illustrates an exemplary replay cine display, in accordance with an embodiment of the invention.

FIG. 2 illustrates an exemplary replay cine display 200, in accordance with an embodiment of the invention. Referring to FIG. 2, the replay cine display 200 may be presented, for example, at a display system 134 of the ultrasound system 100. The replay cine display 200 comprises a display window 210, a selected replay cine sequence 220, and display controls 230. In various embodiments, the display 200 can include image thumbnails 240. As an example, if multiple replay cine clips or other images are available for viewing, the available clips or images can be presented as a group of thumbnails 240 or in any suitable image/clip selection format, such as a list, a drop down menu, a browse pop-up window, and the like.

Still referring to FIG. 2, the replay cine sequence 220 may correspond with the image data being displayed in display window 210. The replay cine sequence 220 may comprise a position marker 222 that identifies the temporal position of the sequence 220 currently being displayed in display window 210. The replay cine sequence 220 may show the primary and secondary image acquisitions integrated into a continuous sequential acquisition viewable at the display system 134. The acquisitions may appear as a single replay cine sequence 220, where secondary image acquisitions may be tagged 224 to provide information as to where in the replay cine sequence 220 the secondary snapshot image acquisition(s) can be found amongst the primary real-time motion ultrasound image data. In various embodiments, the secondary image tags 224 can be selected to view the associated secondary image data. Additionally or alternatively, the secondary image data may be displayed when the position marker 222 reaches the tag 224 during playback of the replay cine sequence 200. In certain embodiments, the display window 210 may comprise multiple windows. For example, the primary image acquisition can be displayed in a first window of the display window 210 and the secondary image acquisition may be displayed in a separate second window of the display window 210. In a representative embodiment, the secondary image tags 224 may provide additional information regarding the secondary image acquisition mode. For example, the exemplary tag 224 in the replay cine sequence 220 of FIG. 2 identifies the secondary image acquisition mode as begin a 3D image acquisition.

The display controls 230 of the replay cine display 200 may comprise controls for interacting with the replay cine sequence 220 and display window 210. For example, the controls 230 can include play, stop, pause, fast forward, rewind, playback speed controls, and the like. The display controls 230 may include controls for adjusting one or more of, for example, the brightness, contrast, and color of the images displayed in window 210. The display controls 230 can be adjusted at the display system 134, such as using a touch screen display, and/or at user input module 130, such as a mousing device, buttons, dials, switches, and/or any suitable user input module 130.

Figure 3:
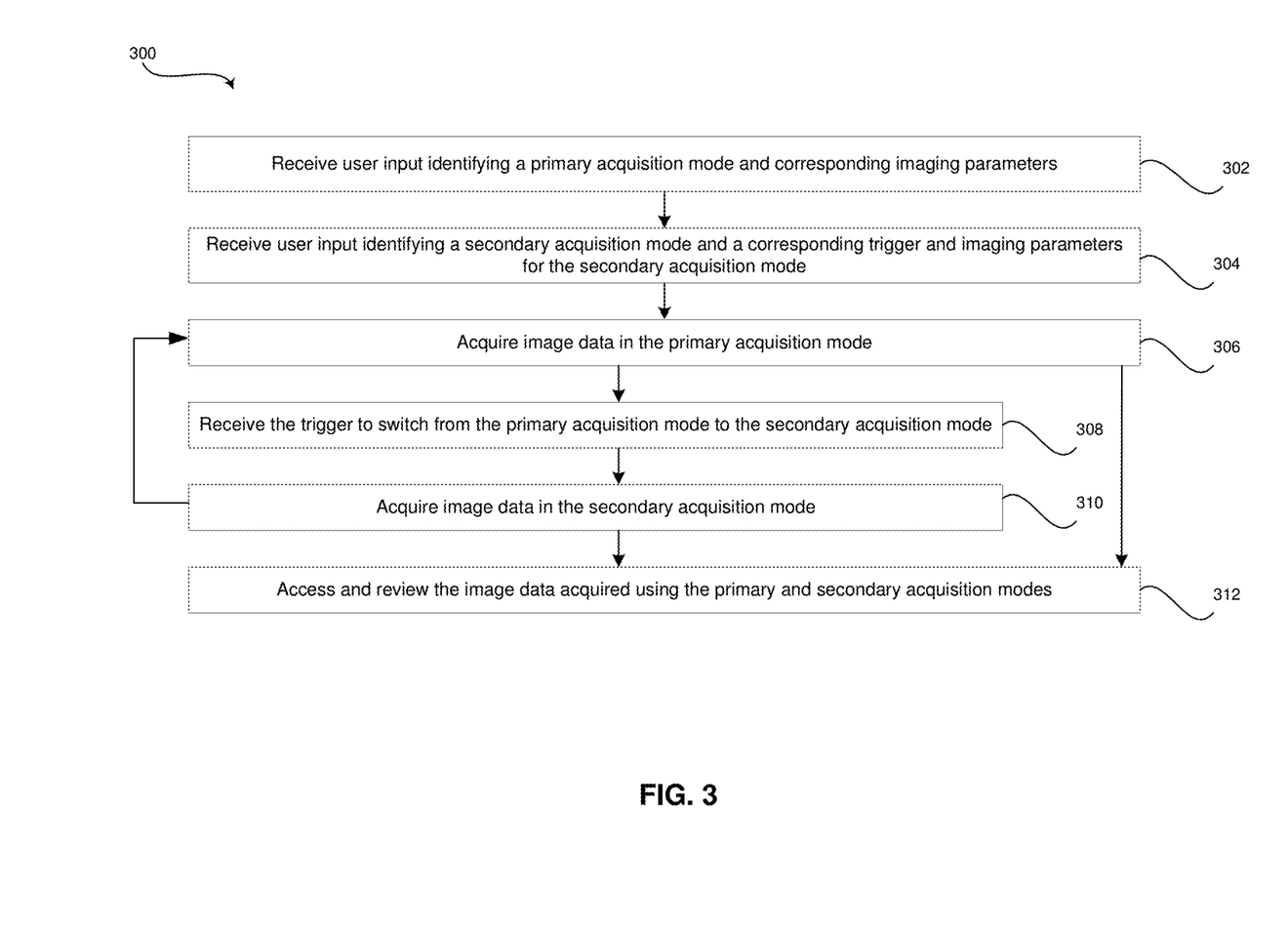
FIG. 3 is a flow chart illustrating exemplary steps that may be utilized for acquiring secondary ultrasound snapshots with primary real-time ultrasound image data, in accordance with an embodiment of the invention.

FIG. 3 is a flow chart illustrating exemplary steps that may be utilized for acquiring secondary ultrasound images with primary real-time ultrasound image data, in accordance with an embodiment of the invention. Referring to FIG. 3, there is shown a flow chart 300 comprising exemplary steps 302 through 312. Certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

In step 302, a user input may be received at the user input module 130 identifying a primary acquisition mode and corresponding imaging parameters. The primary acquisition mode can be, for example, a 2D or 4D real-time motion imaging mode. The imaging parameters may include a depth, width, line density, position of a region-of-interest (ROI), pulse-repetition-frequency (PRF), gain, adaptive gain, transmit focus position, frame averaging, speckle reduction filtering, compounding, a number of compounding angles, or some combination. The imaging parameters may be stored in association with the primary acquisition mode and applied when acquiring the image data in the primary acquisition mode. In various embodiments, one or more of the imaging parameters may be default parameters that may be optionally changed at the user input module 130.

In step 304, a user input may be received at the user input module 130 identifying a secondary acquisition mode, a trigger for switching from the primary acquisition mode to the secondary acquisition mode, and imaging parameters for the secondary acquisition mode. The secondary acquisition modes may include, for example, 2D, 3D, 4D, or STIC style acquisition modes. The secondary acquisition mode may be higher quality than the primary acquisition mode and/or can include an acquisition type that is different than the primary acquisition type. The trigger may be a timer trigger, an automatic trigger, a user trigger, or any suitable trigger for switching from a primary acquisition mode to a secondary acquisition mode. The imaging parameters, such as the image parameters discussed above, may be stored in association with the secondary acquisition mode and applied when acquiring the image data in the secondary acquisition mode. In an exemplary embodiment, one or more of the imaging parameters may be default parameters that may be optionally changed at the user input module 130.

In step 306, the ultrasound system 100 acquires image data in the primary acquisition mode. The ultrasound system 100 acquires the primary image data using the stored primary acquisition mode imaging parameters that can be default parameters and/or parameters obtained at step 302 above. The ultrasound system 100 stores the acquired image data and may display the acquired image data at a display system 134. If the ultrasound examination is completed during step 306, the method 300 may proceed to step 312.

In step 308, the ultrasound system 100 receives a trigger to switch from the primary acquisition mode to the secondary acquisition mode. The trigger can be set-up at step 304 and may be, for example, a timer trigger, an automatic trigger, a user trigger, or any suitable trigger. The timer trigger may switch from a primary image acquisition mode to a secondary acquisition mode at a pre-determined interval that can be set-up at step 304. The automatic trigger may include switching from the primary acquisition mode to the secondary acquisition mode when one or more conditions of the ultrasound system 100 have been satisfied, such as when a heart rate is detected and a real-time motion image is stable, among other things. The user trigger can be a button, switch, or any suitable mechanism that may be activated by a user to initiate the secondary image acquisition.

In step 310, the ultrasound system 100 acquires image data in the secondary acquisition mode. The ultrasound system 100 acquires the secondary acquisition using the stored secondary acquisition mode imaging parameters that can be default parameters and/or parameters obtained at step 304. The ultrasound system 100 may display the acquired image data at a display system 134 and/or may store the acquired image data for later review. The acquired secondary image data may be stored separately from the primary image data or can be integrated with the primary image data to form a single continual image acquisition sequence. In a representative embodiment, the primary image data is tagged to indicate where the secondary image data was acquired. After the secondary image data is acquired, the method 300 returns to step 306 to resume acquiring image data in the primary acquisition mode or proceeds to step 312 if the ultrasound examination is finished.

In step 312, the ultrasound data acquired using the primary and secondary acquisition modes is accessed and viewed at a display system, such as the display system 132 of the ultrasound system 100. For example, with referenced to FIG. 2 above, the workflow for reviewing ultrasound image data acquired in different acquisition modes may include loading a selected replay cine sequence 220 at the replay cine display 200 presented at, for example, the display system 134 of the ultrasound system 100. In various embodiments, the replay cine sequence 220 can be selected from a list or group 240 of available images and/or sequences. Additionally and/or alternatively, all the ultrasound image data from an examination can be integrated into a single continuous replay cine sequence 220. The secondary ultrasound image data can be stored with the primary ultrasound image data as the secondary image data is acquired at step 310 or a display sequence 220 can be generated from separately stored primary and secondary acquisitions, for example, when the replay cine sequence 220 is loaded at the replay cine display 200 for review at step 312.

Display controls 230 of a replay cine display 200 are used to interact with the selected replay cine sequence 220 and the display window 210. For example, a display control 230 may be selected for playing the replay cine sequence 220, causing primary real-time motion acquisition data to be played back and displayed in the display window 210. The images displayed in the window 210 correspond with a position of marker 222 in the replay cine sequence 220. As the position marker 222 advances in the replay cine sequence 220, it reaches a secondary image marker 224 that corresponds with, for example, a higher quality, static, 3D secondary image acquisition. The secondary image acquisition is displayed in window 210 when the position marker 222 reaches secondary image marker 224. After a predetermined period of time or after receiving an instruction at display controls 230, the replay cine sequence 220 continues playing the primary real-time motion acquisition data appearing after the secondary image marker 224 in the display window 210. The position marker 222 continues advancing in the replay cine sequence 220 as the sequence 220 is played back in the display window 210. The exemplary workflow for reviewing ultrasound image data acquired in multiple image acquisition modes at step 312 improves visualization of the image data by presenting the image data acquired in the different image acquisition modes as a single continual acquisition on a display system 134.

Aspects of the present invention provide a system 100 and method 300 for supporting secondary snapshot image acquisition while acquiring primary real-time motion ultrasound image data. In accordance with various embodiments of the invention, a method 300 comprises acquiring 306 first image data at an ultrasound system 100 in a primary acquisition mode based on primary acquisition mode imaging parameters. The method 300 comprises receiving 308 a trigger to switch from the primary acquisition mode to a secondary acquisition mode. The method 300 comprises acquiring 310 second image data at the ultrasound system 100 in a secondary acquisition mode based on secondary acquisition mode imaging parameters in response to the trigger. The method 300 comprises displaying 312 a replay cine sequence 220 comprising the first image data and the second image data. The replay cine sequence 220 comprises a tag 224 identifying the second image data in the replay cine sequence 220.

In a representative embodiment, the method 300 comprises receiving 302 user input at a user input module 130 identifying one or more of the primary acquisition mode and the primary acquisition mode imaging parameters prior to acquiring 306 the first image data. In various embodiments, the method 300 comprises receiving 304 user input at a user input module 130 identifying one or more of the secondary acquisition mode, the trigger, and the secondary acquisition mode imaging parameters prior to acquiring 306 the first image data, receiving 308 the trigger, and acquiring 310 the second image data.

In certain embodiments, the trigger comprises one or more of a timer trigger configured to activate at one or more predetermined times, an automatic trigger configured to activate when at least one condition is detected in one or more of the first image data and the second image data, and a user trigger configured to activate based on an input received at a user input module 130. In a representative embodiment, the primary acquisition mode is one of a two-dimensional (2D) real-time motion imaging mode, and a four-dimensional (4D) imaging mode. In various embodiments, the secondary acquisition mode is one of a static two-dimensional (2D) imaging mode, a static three-dimensional (3D) imaging mode, a four-dimensional (4D) imaging mode, and a spatio-temporal image correlation (STIC) style acquisition imaging mode. In certain embodiments, the second image data is higher quality than the first image data.

In various embodiments, the method 300 comprises playing back 312 the replay cine sequence 220 in a display window 210 of a replay cine display 200. The replay cine sequence 220 comprises a position marker 222 identifying a current temporal position corresponding with the replay cine sequence 220 being played back in the display window 210. In a representative embodiment, the method 300 comprises presenting 312 the second image data of the replay cine sequence 220 in the display window 210 of the replay cine display 200 when one or more of the position marker 222 reaches the tag 224 in the replay cine sequence 220, or a user input is received at a user input module 130 selecting that tag 224 in the replay cine sequence 220.

In accordance with various embodiments of the invention, a system comprises an ultrasound device operable acquire first image data in a primary acquisition mode based on primary acquisition mode imaging parameters, and acquire second image data in a secondary acquisition mode based on secondary acquisition mode imaging parameters. The system comprises a processor 132 operable to detect a trigger to switch from the primary acquisition mode to a secondary acquisition mode. The system comprises a display system 134 operable to display a replay cine sequence 220 comprising the first image data and the second image data. The second image data is acquired in response to the detected trigger. The replay cine sequence 220 comprises a tag 224 identifying the second image data in the replay cine sequence 220.

In a representative embodiment, the system comprises a user input module 130 configured to receive one or more of user input identifying one or more of the primary acquisition mode and the primary acquisition mode imaging parameters prior to acquiring the first image data; user input identifying one or more of the secondary acquisition mode, the trigger, and the secondary acquisition mode imaging parameters prior to acquiring the first image data, detecting the trigger, and acquiring the second image data; and, user input provided as the trigger to the processor 132 to switch from the primary acquisition mode to a secondary acquisition mode.

In certain embodiments, the trigger comprises one or more of a timer trigger configured to activate at one or more predetermined times, an automatic trigger configured to activate when at least one condition is detected in one or more of the first image data and the second image data, and a user trigger configured to activate based on an input received at a user input module 130. In various embodiments, the primary acquisition mode is one of a two-dimensional (2D) real-time motion imaging mode, and a four-dimensional (4D) imaging mode. In a representative embodiment, the secondary acquisition mode is one of a static two-dimensional (2D) imaging mode, a static three-dimensional (3D) imaging mode, a four-dimensional (4D) imaging mode, and a spatio-temporal image correlation (STIC) style acquisition imaging mode. In certain embodiments, the second image data is higher quality than the first image data.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set { (x), (y), (x, y)}. As another example, "x, y, and/or z" means any element of the seven-element set { (x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for supporting acquisition of secondary ultrasound image snapshots with primary real-time ultrasound image data.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method, comprising:
    acquiring first image data at an ultrasound system in a primary acquisition mode based on primary acquisition mode imaging parameters;
    receiving a trigger to switch from the primary acquisition mode to a secondary acquisition mode;
    acquiring second image data at the ultrasound system in a secondary acquisition mode based on secondary acquisition mode imaging parameters in response to the trigger;
    generating a replay cine sequence comprising the first image data and the second image data, wherein the replay cine sequence comprises a tag identifying the second image data in the replay cine sequence; and
    displaying the replay cine sequence.

2. The method according to claim 1, comprising receiving user input at a user input module identifying one or more of the primary acquisition mode and the primary acquisition mode imaging parameters prior to acquiring the first image data.

3. The method according to claim 1, comprising receiving user input at a user input module identifying one or more of the secondary acquisition mode, the trigger, and the secondary acquisition mode imaging parameters prior to acquiring the first image data, receiving the trigger, and acquiring the second image data.

4. The method according to claim 3, wherein the trigger comprises one or more of:
    a timer trigger configured to activate at one or more predetermined times,
    an automatic trigger configured to activate when at least one condition is detected in one or more of the first image data and the second image data, and
    a user trigger configured to activate based on an input received at a user input module.

5. The method according to claim 1, wherein the primary acquisition mode is one of:
    a two-dimensional (2D) real-time motion imaging mode, and
    a four-dimensional (4D) imaging mode.

6. The method according to claim 1, wherein the secondary acquisition mode is one of:
    a static two-dimensional (2D) imaging mode,
    a static three-dimensional (3D) imaging mode,
    a four-dimensional (4D) imaging mode, and
    a spatio-temporal image correlation (STIC) style acquisition imaging mode.

7. The method according to claim 1, wherein the second image data is acquired at a higher transmit power than the first image data.

8. The method according to claim 1, comprising playing back the replay cine sequence in a display window of a replay cine display, wherein the replay cine sequence comprises a position marker identifying a current temporal position corresponding with the replay cine sequence being played back in the display window.

9. The method according to claim 8, comprising presenting the second image data of the replay cine sequence in the display window of the replay cine display when one or more of:

the position marker reaches the tag in the replay cine sequence, or a user input is received at a user input module selecting that tag in the replay cine sequence.

10. A system, comprising:

an ultrasound device operable to:

acquire first image data in a primary acquisition mode based on primary acquisition mode imaging parameters, and acquire second image data in a secondary acquisition mode based on secondary acquisition mode imaging parameters;

a processor operable to:

detect a trigger to switch from the primary acquisition mode to a secondary acquisition mode, and generate a replay cine sequence comprising the first image data and the second image data, wherein the replay cine sequence comprises a tag identifying the second image data in the replay cine sequence; and a display system operable to display the replay cine sequence, wherein the second image data is acquired in response to the detected trigger.

11. The system according to claim 10, comprising a user input module configured to receive one or more of:

user input identifying one or more of the primary acquisition mode and the primary acquisition mode imaging parameters prior to acquiring the first image data, user input identifying one or more of the secondary acquisition mode, the trigger, and the secondary acquisition mode imaging parameters prior to acquiring the first image data, detecting the trigger, and acquiring the second image data, and user input provided as the trigger to the processor to switch from the primary acquisition mode to a secondary acquisition mode.

12. The system according to claim 10, wherein the trigger comprises one or more of:

a timer trigger configured to activate at one or more predetermined times, an automatic trigger configured to activate when at least one condition is detected in one or more of the first image data and the second image data, and a user trigger configured to activate based on an input received at a user input module.

13. The system according to claim 11, wherein the primary acquisition mode is one of:

a two-dimensional (2D) real-time motion imaging mode, and a four-dimensional (4D) imaging mode.

14. The system according to claim 11, wherein the secondary acquisition mode is one of:

a static two-dimensional (2D) imaging mode, a static three-dimensional (3D) imaging mode, a four-dimensional (4D) imaging mode, and a spatio-temporal image correlation (STIC) style acquisition imaging mode.

15. The system according to claim 11, wherein the second image data is acquired at a higher transmit power than the first image data.

16. A non-transitory computer readable medium having stored thereon, a computer program having at least one code section, the at least one code section being executable by a machine for causing the machine to perform steps comprising:

acquiring first image data in a primary acquisition mode based on primary acquisition mode imaging parameters;

receiving a trigger to switch from the primary acquisition mode to a secondary acquisition mode;

acquiring second image data in a secondary acquisition mode based on secondary acquisition mode imaging parameters in response to the trigger;

generating a replay cine sequence comprising the first image data and the second image data, wherein the replay cine sequence comprises a tag identifying the second image data in the replay cine sequence; and displaying the replay cine sequence.

17. The non-transitory computer readable medium according to claim 16, comprising receiving one or more of:

user input identifying one or more of the primary acquisition mode and the primary acquisition mode imaging parameters prior to acquiring the first image data, and user input identifying one or more of the secondary acquisition mode, the trigger, and the secondary acquisition mode imaging parameters prior to acquiring the first image data, receiving the trigger, and acquiring the second image data.

18. The non-transitory computer readable medium according to claim 17, wherein the trigger comprises one or more of:

a timer trigger configured to activate at one or more predetermined times, an automatic trigger configured to activate when at least one condition is detected in one or more of the first image data and the second image data, and a user trigger configured to activate based on an input received at a user input module.

19. The non-transitory computer readable medium according to claim 16, comprising playing back the replay cine sequence in a display window of a replay cine display, wherein the replay cine sequence comprises a position marker identifying a current temporal position corresponding with the replay cine sequence being played back in the display window.

20. The non-transitory computer readable medium according to claim 19, comprising presenting the second image data of the replay cine sequence in the display window of the replay cine display when one or more of:

the position marker reaches the tag in the replay cine sequence, or a user input is received at a user input module selecting that tag in the replay cine sequence.

* * * * *